(12) United States Patent
Govari et al.

(10) Patent No.: US 11,589,772 B2
(45) Date of Patent: Feb. 28, 2023

(54) PROBE WITH RADIOPAQUE TAG

(71) Applicant: BIOSENSE WEBSTER (ISRAEL) LTD., Yokneam (IL)

(72) Inventors: Assaf Govari, Haifa (IL); Yehuda Algawi, Binyamina (IL); Vadim Gliner, Yokneam (IL); Ilya Sitnitsky, Nahariya (IL); Andres Claudio Altmann, Haifa (IL)

(73) Assignee: Biosense Webster (Israel) Ltd., Yokneam (IL)

( * ) Notice: Subject to any disclaimer, the term of this patent is extended or adjusted under 35 U.S.C. 154(b) by 356 days.

(21) Appl. No.: 16/797,619

(22) Filed: Feb. 21, 2020

(65) Prior Publication Data
US 2020/0367786 A1 Nov. 26, 2020

Related U.S. Application Data

(60) Provisional application No. 62/852,272, filed on May 23, 2019.

(51) Int. Cl.
*A61B 5/06* (2006.01)
*A61B 34/20* (2016.01)
*A61B 90/00* (2016.01)

(52) U.S. Cl.
CPC .............. *A61B 5/064* (2013.01); *A61B 34/20* (2016.02); *A61B 90/36* (2016.02); *A61B 90/39* (2016.02);

(Continued)

(58) Field of Classification Search
CPC ........ A61B 2090/364; A61B 2090/376; A61B 2090/3966; A61B 2090/3995;
(Continued)

(56) References Cited

U.S. PATENT DOCUMENTS 5,558,091 A * 9/1996 Acker .................... A61B 5/103
324/207.13
6,317,621 B1 11/2001 Graumann et al.
(Continued)

OTHER PUBLICATIONS

International Search Report dated Aug. 6, 2020 from corresponding PCT Patent Application No. PCT/IB2020/053937.

*Primary Examiner* — Amelie R Davis
(74) *Attorney, Agent, or Firm* — Frost Brown Todd LLP

(57) ABSTRACT

A medical procedure system, including a medical instrument to be inserted into a body part, and including position-tracking transducers to provide position signals, a distal end, and at least one radiopaque marker, a position tracking sub-system to compute a position including at least one location and orientation of the distal end in a position-tracking sub-system coordinate frame responsively to the position signals, a fluoroscope to capture fluoroscopic images of an interior of the body part and the radiopaque marker(s), and a registration sub-system to render, to a display, the captured fluoroscopic images including at least one marker-image of the radiopaque marker(s), and at least one graphical representation indicative of the computed position of the distal end, receive user-alignment input aligning the graphical representation(s) with the marker-image(s), and register the position-tracking sub-system coordinate frame with a coordinate frame of the fluoroscope responsively to the received user-alignment input.

24 Claims, 14 Drawing Sheets

(52) U.S. Cl.
CPC ........... *A61B 2034/2046* (2016.02); *A61B 2034/2068* (2016.02); *A61B 2090/376* (2016.02); *A61B 2090/3966* (2016.02)

(58) Field of Classification Search
CPC ........... A61B 34/20; A61B 5/065; A61B 6/12; A61B 90/36; A61B 90/37; A61B 90/39; A61B 2034/2046
See application file for complete search history.

(56) References Cited

U.S. PATENT DOCUMENTS

| | | |
|---|---|---|
| 2014/0114173 A1 | 4/2014 | Bar-Tal et al. |
| 2016/0007842 A1 | 1/2016 | Govari et al. |
| 2017/0151027 A1 | 6/2017 | Walker et al. |
| 2018/0325610 A1 | 11/2018 | Cameron et al. |
| 2019/0000372 A1 | 1/2019 | Gullotti et al. |

\* cited by examiner

PROBE WITH RADIOPAQUE TAG

RELATED APPLICATION INFORMATION

The present application claims benefit of U.S. Provisional Patent Application No. 62/852,272 of Govari, et al., filed on May 23, 2019.

FIELD OF THE INVENTION

The present invention relates to medical instruments, and in particular, but not exclusively to, tracking positions of medical instruments.

BACKGROUND

Medical images such as CT scans are often captured prior to a medical procedure and then registered with a position tracking coordinate system of a medical instrument so that the medical instrument may be displayed together with the medical scan to aid navigation of the medical instrument in a body-part by a physician.

By way of example, U.S. Pat. No. 6,317,621 to Graumann, et al., describes a method and apparatus for catheter navigation in three-dimensional vascular tree exposures, particularly for intercranial application, the catheter position is detected and mixed into the 3D image of the preoperatively scanned vascular tree reconstructed in a navigation computer and an imaging (registering) of the 3D patient coordination system ensues on the 3D image coordination system prior to the intervention using a number of markers placed on the patient's body, the position of these markers being registered by the catheter. The markers of a C-arm x-ray device for 3D angiography are detected in at least two 2D projection images, from which the 3D angiogram is calculated, and are projected back on to the imaged subject in the navigation computer and are brought into relation to the marker coordinates in the patient coordinate system, using projection matrices applied to the respective 2D projection images, these matrices already having been determined for the reconstruction of the 3D volume set of the vascular tree.

US Patent Publication 2014/0114173, issued as U.S. Pat. No. 10,441,236 on Oct. 15, 2019, of Bar-tal, et al., describes a coordinate system registration module, including radiopaque elements arranged in a fixed predetermined pattern and configured, in response to the radiopaque elements generating a fluoroscopic image, to define a position of the module in a fluoroscopic coordinate system of reference. The module further includes one or more connections configured to fixedly connect the module to a magnetic field transmission pad at a predetermined location and orientation with respect to the pad, so as to characterize the position of the registration module in a magnetic coordinate system of reference defined by the magnetic field transmission pad.

SUMMARY

There is provided in accordance with an embodiment of the present disclosure, a medical procedure system, including a medical instrument configured to be inserted into a body part of a living subject, and including position-tracking transducers configured to provide position signals, a shaft, a distal end, and at least one radiopaque marker, a position tracking sub-system configured to compute a position including at least one location and an orientation of the distal end of the medical instrument in a position-tracking sub-system coordinate frame responsively to the position signals, a fluoroscope configured to capture fluoroscopic images of an interior of the body part and the at least one radiopaque marker of the medical instrument over time, a display, and a registration sub-system configured to render, to the display, the captured fluoroscopic images including at least one marker-image of the at least one radiopaque marker, and at least one graphical representation indicative of the computed position of the distal end, receive user-alignment input aligning the at least one graphical representation with the at least one marker-image, and register the position-tracking sub-system coordinate frame with a coordinate frame of the fluoroscope responsively to the received user-alignment input.

Further in accordance with an embodiment of the present disclosure the distal end includes an element which is configured to extend away from an axis of the shaft, the at least one radiopaque marker includes a first radiopaque marker disposed on the shaft, and a second radiopaque marker disposed on the element which is configured to extend away from the axis of the shaft, the position tracking sub-system is configured to compute a first position including a first location and an orientation of the distal end of the medical instrument in the position-tracking sub-system coordinate frame responsively to at least one of the position signals, and a second position including a second location of the distal end of the medical instrument in the position-tracking sub-system coordinate frame responsively to at least one of the position signals, and the registration sub-system is configured to render, to the display, the captured fluoroscopic images including a first marker-image of the first radiopaque marker, a second marker-image of the second radiopaque marker, a first graphical representation indicative of the computed first position of the distal end, and a second graphical representation indicative of the computed second position of the distal end, receive user-alignment input aligning the first graphical representation with the first marker-image, and the second graphical representation with the second marker-image.

Still further in accordance with an embodiment of the present disclosure the position-tracking transducers include a first coil disposed coaxially with the shaft.

Additionally, in accordance with an embodiment of the present disclosure the first radiopaque marker includes a radiopaque cylinder.

Moreover, in accordance with an embodiment of the present disclosure the first coil is wound on the radiopaque cylinder.

Further in accordance with an embodiment of the present disclosure the position-tracking transducers includes a second coil disposed orthogonally to the first coil.

Still further in accordance with an embodiment of the present disclosure the element which is configured to extend away from the axis of the shaft is included in an inflatable balloon.

Additionally, in accordance with an embodiment of the present disclosure the first radiopaque marker includes a radiopaque cylinder, the first coil being wound on the radiopaque cylinder, and the position-tracking transducers including a second coil disposed orthogonally to the first coil.

Moreover, in accordance with an embodiment of the present disclosure the element which is configured to extend away from the axis of the shaft is included in an elongated element including an electrode.

Further in accordance with an embodiment of the present disclosure the position-tracking transducers include the electrode.

Still further in accordance with an embodiment of the present disclosure the second radiopaque marker is co-located with the electrode.

Additionally, in accordance with an embodiment of the present disclosure the at least one radiopaque marker includes a cylinder with a longitudinal gap.

There is also provided in accordance with another embodiment of the present disclosure, a medical procedure method, including inserting a medical instrument into a body part of a living subject, computing a position including at least one location and an orientation of a distal end of the medical instrument in a position-tracking sub-system coordinate frame responsively to position signals provided by position-tracking transducers of the medical instrument, capturing, using a fluoroscope, fluoroscopic images of an interior of the body part and at least one radiopaque marker of the medical instrument over time, rendering, to a display, the captured fluoroscopic images including at least one marker-image of the at least one radiopaque marker, and at least one graphical representation indicative of the computed position of the distal end, receiving user-alignment input aligning the at least one graphical representation with the at least one marker-image, and registering the position-tracking sub-system coordinate frame with a coordinate frame of the fluoroscope responsively to the received user-alignment input.

Moreover in accordance with an embodiment of the present disclosure the distal end includes an element which is configured to extend away from an axis of a shaft of the medical instrument, the at least one radiopaque marker includes a first radiopaque marker disposed on the shaft, and a second radiopaque marker disposed on the element which is configured to extend away from the axis of the shaft, the method further including computing a first position including a first location and an orientation of the distal end of the medical instrument in the position-tracking sub-system coordinate frame responsively to at least one of the position signals, computing a second position including a second location of the distal end of the medical instrument in the position-tracking sub-system coordinate frame responsively to at least one of the position signals, rendering, to the display, the captured fluoroscopic images including a first marker-image of the first radiopaque marker, a second marker-image of the second radiopaque marker, a first graphical representation indicative of the computed first position of the distal end, and a second graphical representation indicative of the computed second position of the distal end, and receiving user-alignment input aligning the first graphical representation with the first marker-image, and the second graphical representation with the second marker-image.

Further in accordance with an embodiment of the present disclosure the position-tracking transducers include a first coil disposed coaxially with the shaft.

Still further in accordance with an embodiment of the present disclosure the first radiopaque marker includes a radiopaque cylinder.

Additionally, in accordance with an embodiment of the present disclosure the first coil is wound on the radiopaque cylinder.

Moreover, in accordance with an embodiment of the present disclosure the position-tracking transducers includes a second coil disposed orthogonally to the first coil.

Further in accordance with an embodiment of the present disclosure the element which is configured to extend away from the axis of the shaft is included in an inflatable balloon.

Still further in accordance with an embodiment of the present disclosure the first radiopaque marker includes a radiopaque cylinder, the first coil being wound on the radiopaque cylinder, and the position-tracking transducers including a second coil disposed orthogonally to the first coil.

Additionally, in accordance with an embodiment of the present disclosure the element which is configured to extend away from the axis of the shaft is included in an elongated element including an electrode.

Moreover, in accordance with an embodiment of the present disclosure the position-tracking transducers include the electrode.

Further in accordance with an embodiment of the present disclosure the second radiopaque marker is co-located with the electrode.

Still further in accordance with an embodiment of the present disclosure the at least one radiopaque marker includes a cylinder with a longitudinal gap.

BRIEF DESCRIPTION OF THE DRAWINGS

The present invention will be understood from the following detailed description, taken in conjunction with the drawings in which.

DESCRIPTION OF EXAMPLE EMBODIMENTS

Overview

Figure 1:
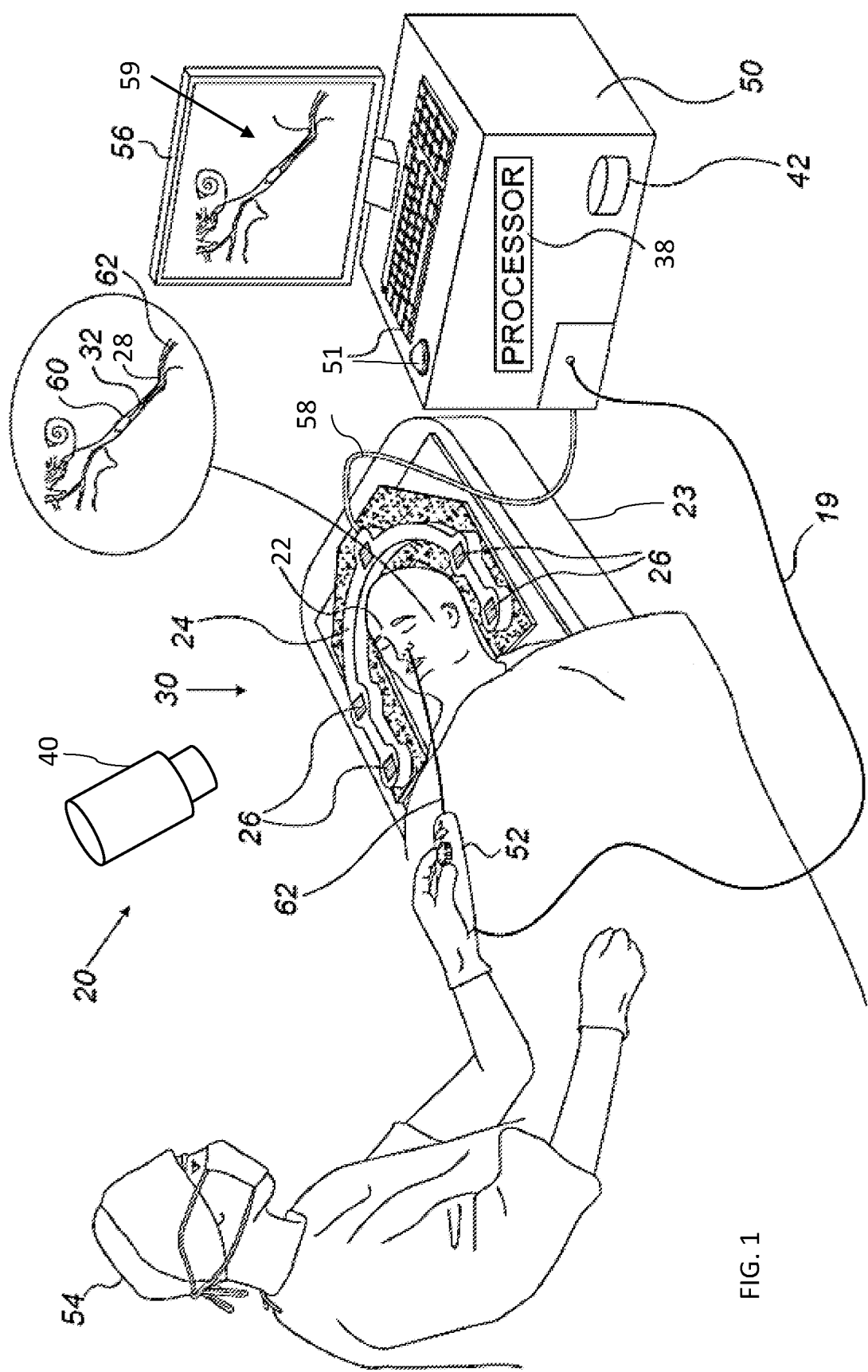
FIG. 1 is a partly pictorial, partly block diagram view of a medical procedure system constructed and operative in accordance with an embodiment of the present invention.

As mentioned previously, medical images such as CT scans are often captured prior to a medical procedure and then registered with a position tracking coordinate system of a medical instrument so that the medical instrument may be displayed together with the medical scan to aid navigation of the medical instrument in a body-part by a physician.

In some circumstances, for example, due to a medical procedure becoming more complicated than originally anticipated, or for other reasons, a physician may want to introduce a fluoroscope to capture fluoroscopic images during the medical procedure. In order to see how the body parts are moving with respect to the medical tool, the coordinate frame of the fluoroscope needs to be registered with the coordinate frame of the tracking system which is tracking the medical instrument. Mid-procedure registration may be problematic. For example, how can registration be performed quickly and accurately so as not to add delays to the medical procedure and to provide an accurate picture of the body part with respect to the moving medical instrument.

Embodiments of the present invention provide a medical procedure system with the capability of introducing a fluoroscope mid-procedure and quickly and accurately registering the coordinate frame of the fluoroscope with the coordinate frame of a position-tracking sub-system which is tracking the medical instrument using transducers. Once the two coordinate frames have been successfully registered, the fluoroscopic images can be displayed with a representation of the medical instrument superimposed thereon to accurately show the position of the moving medical instrument with respect to the real-time fluoroscopic images of the body part.

The medical instrument includes radiopaque markers which are placed on the medical instrument within a given special relationship of the position-tracking transducers of the medical instrument and enable registration of both location, orientation including roll of the two coordinate frames, as will be described below in more detail.

When a fluoroscope is introduced, the radiopaque markers are seen in captured fluoroscopic images. The radiopaque markers provide enough information to indicate locations and an orientation including roll of the medical instrument in the fluoroscopic images. The position of the medical instrument is also computed from position signals provided by the position-tracking transducers and provides at least one location and orientation including roll of the medical instrument in the coordinate frame of the position-tracking sub-system.

In one embodiment, the medical instrument includes a shaft and an inflatable balloon. The shaft includes a first coil wound upon a radiopaque cylinder which is coaxial with the shaft and a second coil disposed orthogonally to the first coil. The balloon includes a radiopaque marker disposed thereon. The radiopaque cylinder indicates a location and orientation (excluding roll) of the medical instrument in the fluoroscopic images. The radiopaque marker disposed on the balloon indicates a roll of the medical instrument in the fluoroscopic images. The first and second coils together provide signals indicative of a location and orientation (including roll) of the shaft. A cylinder defined by the location and orientation of the first coil is superimposed over one of the fluoroscopic images. An element defined by the roll computed by the signal of the second coil is also superimposed over the fluoroscopic image. A user then manipulates the superimposed cylinder and the element to align them with the image of the radiopaque cylinder and balloon radiopaque marker, respectively. The user alignment input defines the differences between the fluoroscope coordinate frame and the position-tracking sub-system coordinate frame. The user alignment input is then used to register the two coordinate frames with each other.

In other embodiments the coil is not wound over the radiopaque cylinder, but it wound over another portion of the medical instrument and has a known spatial relationship to the radiopaque cylinder.

In another embodiment, a probe having a shaft and prongs extending from the shaft may be used. The probe includes a coil wound over a radiopaque cylinder disposed in the shaft, typically coaxially with the shaft. Signals from the coil may be used to compute a location and orientation (excluding roll) of the probe. The prongs also include a plurality of electrodes. One of the electrodes may be used to determine a roll of the probe. A radiopaque marker may also be disposed on one of the prongs, for example, adjacent to, or co-located with, the electrode used to determine the roll of the probe. Alternatively, the roll may be determined using a second coil disposed orthogonally to the abovementioned coil, which is wound on the radiopaque cylinder. A cylinder defined by the location and orientation of the coaxial coil is superimposed over the fluoroscopic images. An element defined by the roll computed by the signal of the second coil is also superimposed over the fluoroscopic image. A user then manipulates the superimposed cylinder and the element to align them with the image of the radiopaque cylinder and prong radiopaque marker, respectively. The user alignment input defines the differences between the fluoroscope coordinate frame and the position-tracking sub-system coordinate frame. The user alignment input is then used to register the two coordinate frames with each other.

The medical instrument is not limited to including a balloon or a plurality of prongs, but may include any medical instrument having a distal end with an element which extends away from an axis of the shaft so as to provide meaningful data about the roll of the medical instrument based on the radiopaque marker disposed on the element which extends away from the axis of the shaft. The extent to which the element needs to extend away from the axis of the shaft may depend on the desired registration accuracy.

In some embodiments, a single radiopaque marker may be used to align location, orientation including roll. For example, the radiopaque marker may include a cylinder with a longitudinal gap. A cylinder with a similarly sized longitudinal gap defined by a location and orientation (including roll) computed from signals provided by the coaxial coil and an orthogonally placed coil is superimposed over one of the fluoroscopic images. A user then manipulates the superimposed cylinder with the image of the radiopaque cylinder aligning the cylinders including the longitudinal gaps of the cylinders. The user alignment input defines the differences between the fluoroscope coordinate frame and the position-tracking sub-system coordinate frame. The user alignment input is then used to register the two coordinate frames with each other.

System Description

Documents incorporated by reference herein are to be considered an integral part of the application except that, to the extent that any terms are defined in these incorporated documents in a manner that conflicts with definitions made explicitly or implicitly in the present specification, only the definitions in the present specification should be considered.

Figure 2:
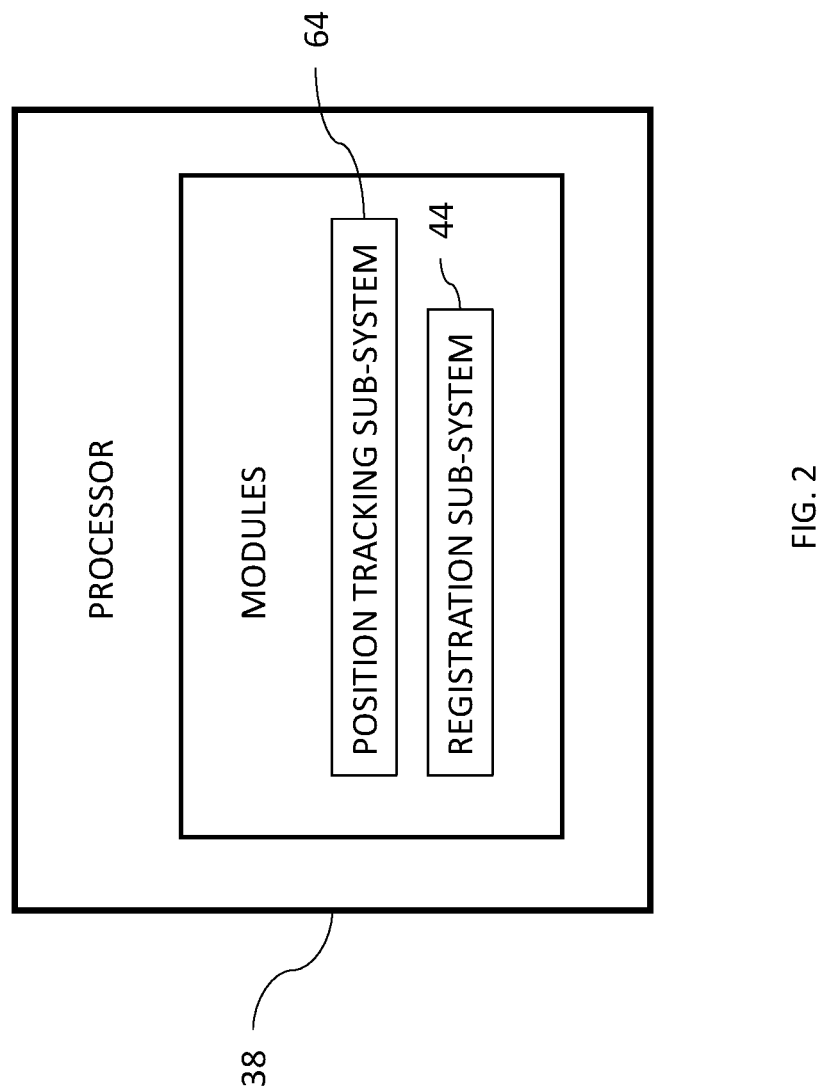
FIG. 2 is a block diagram of a processor of the system of FIG. 1.

Turning now to the drawings, reference is now made to FIG. 1, which is a partly pictorial, partly block diagram view of a medical procedure system 20 constructed and operative in accordance with an embodiment of the present invention, and to FIG. 2, which is a block diagram of a processor of the system of FIG. 1. The medical procedure system 20 is typically used during an invasive and/or investigative procedure on a nasal sinus or another body part (such as the brain or heart) of a patient 22.

For the procedure, a magnetic field radiation assembly 24 may be positioned behind and/or around the head of the patient 22, for example by fixing the assembly 24 to a bed 23 upon which the patient 22 is lying. The magnetic field radiation assembly 24 in the pictured example comprises five magnetic field radiators 26, which are fixed in a horseshoe shaped frame, the frame being positioned beneath or around the patient 22 so that the magnetic field radiators 26 surround the head of the patient 22. Alternatively, smaller or larger numbers of radiators 26 may be used, in various different configurations. The magnetic field radiators 26 are configured to radiate alternating magnetic fields at respective frequencies into a region 30 where the body part is located, in proximity to the magnetic field radiation assembly 24 and which includes the head of patient 22.

The alternating magnetic fields induce signals in position-tracking transducers 32. The position-tracking transducers 32 are shown disposed on a medical instrument 28 in order to track a position of the medical instrument 28. In some embodiments, the medical instrument 28 may include an inflatable balloon 60. By way of example only, the medical instrument 28 may include any one or more of the following, a probe for inserting into the body-part, an endoscope, and/or a surgical tool such as an ENT tool, suction tool, microdebrider, shaver, and/or grasper.

The position of a distal end 62 of the medical instrument 28 may be tracked using a position-tracking sub-system 64, which tracks position and orientation coordinates of the position-tracking transducers 32 fitted at the distal end 62. The position-tracking transducers 32 are configured to output signals that are indicative of the position of the transducers 32. The signals are processed by the position-tracking sub-system 64 running on processor 38 to track the position of the distal end 62 of the medical instrument 28. In embodiments, where the position-tracking sub-system 64 is a magnetic tracking sub-system, the position-tracking transducers 32 includes at least one coil, and typically two or three orthogonally placed coils. In other embodiments, the position-tracking sub-system 64 may be an electrically-based tracking sub-system using multiple head surface electrodes to track the position of the medical instrument 28 based on a signal emitted by at least one electrode (comprised in the position-tracking transducer 32) of the medical instrument 28. The position-tracking sub-system 64 may be implemented using any suitable location tracking sub-system, for example, but not limited to, an ultrasound-based tracking system where the position-tracking transducers 32 includes at least one ultrasound transducer. Using the position-tracking sub-system 64, a physician 54 advances the distal end 62 of the medical instrument 28 in a body-part, described in more detail below.

As described in more detail below, position-tracking transducers 32 are affixed to the medical instrument 28, and determination of the location and orientation of the position-tracking transducers 32 enables tracking the location and orientation of the distal end 62 (or other location) of the medical instrument 28, that may be reversibly inserted into a body-part of the patient 22 (the living subject).

A system using magnetic field radiators, such as the magnetic field radiators 26, for tracking an entity inserted into a patient is described in US Patent Publication 2016/0007842, issued as U.S. Pat. No. 10,772,489 on Sep. 15, 2020, of Govari et al., which is incorporated herein by reference. In addition, the Carto® system produced by Biosense Webster of 33 Technology Drive, Irvine, Calif. 92618 USA, uses a tracking system similar to that described herein for finding the location and orientation of a coil in a region irradiated by magnetic fields.

Elements of system 20, including radiators 26, may be controlled by the processor 38, which comprises a processing unit communicating with one or more memories 42. Typically, the elements may be connected by cables to the processor 38, for example, radiators 26 may be connected by a cable 58 to the processor 38. Alternatively, or additionally, the elements may be coupled wirelessly to the processor 38. The processor 38 may be mounted in a console 50, which comprises operating controls 51 that typically include a keypad and/or a pointing device such as a mouse or trackball. The console 50 also connects to other elements of the medical procedure system 20, such as a proximal end 52 of the medical instrument 28 via a cable 19. A physician 54 uses the operating controls 51 to interact with the processor 38 while performing the procedure, and the processor 38 may present results produced by system 20 on a display 56.

In some embodiments, prior to performing the medical procedure, CT images of the patient 22 are acquired. The CT images are stored in the memory 42 for subsequent retrieval by the processor 38. In FIG. 1, the display 56 is shown displaying a view 59 of a previous CT scan (or other suitable scan) which may be used as an aid for the physician 54 to guide the medical instrument 28 in the body-part. The CT images may be registered with the magnetic coordinate system so that a representation of the medical instrument 28 may be displayed with the CT images on the display 56.

In practice, some or all of these functions of the processor 38 may be combined in a single physical component or, alternatively, implemented using multiple physical components. These physical components may comprise hard-wired or programmable devices, or a combination of the two. In some embodiments, at least some of the functions of the processor may be carried out by a programmable processor under the control of suitable software. This software may be downloaded to a device in electronic form, over a network, for example. Alternatively, or additionally, the software may be stored in tangible, non-transitory computer-readable storage media, such as optical, magnetic, or electronic memory.

The medical procedure system 20 may also include a fluoroscope 40 for capturing fluoroscopic images. The medical procedure system 20 also includes a registration sub-system 44 running on the processor 38. The fluoroscope 40 and the registration sub-system 44 are described in more detail below with reference to FIGS. 7-14.

Figure 3:
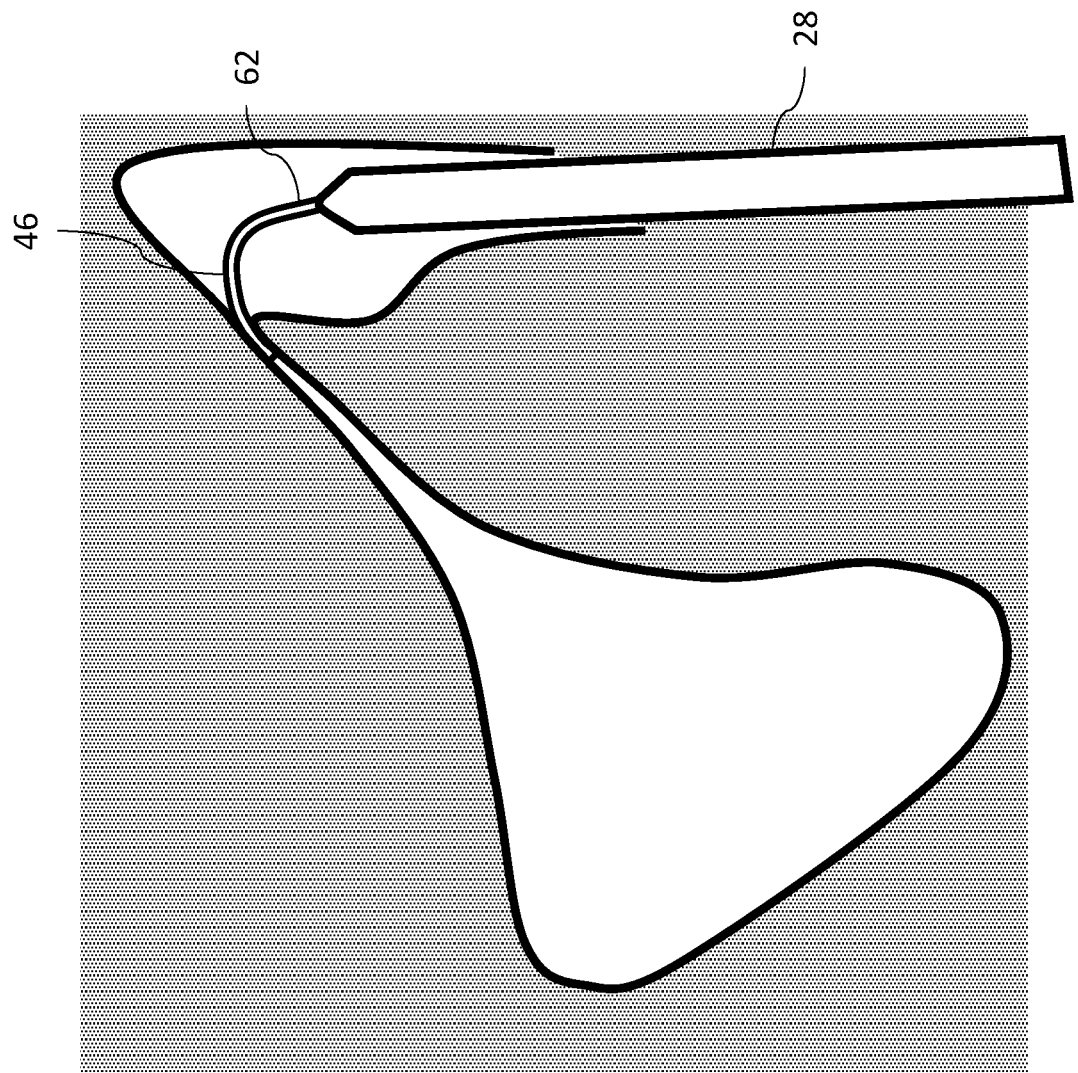
FIG. 3 is a schematic view of a medical instrument of the system of FIG. 1 being inserted into a body-part of a living subject.

Reference is now made to FIG. 3, which is a schematic view of the medical instrument 28 of the system 20 of FIG. 1 being inserted into a body-part of a living subject. The distal end 62 of the medical instrument 28 is shown being inserted into a sinus cavity of the patient 22. FIG. 3 shows that the medical instrument 28 includes a guide 46. The guide 46 may be fixed in multiple configurations ranging from straight to a number of curved formations.

Figure 4:
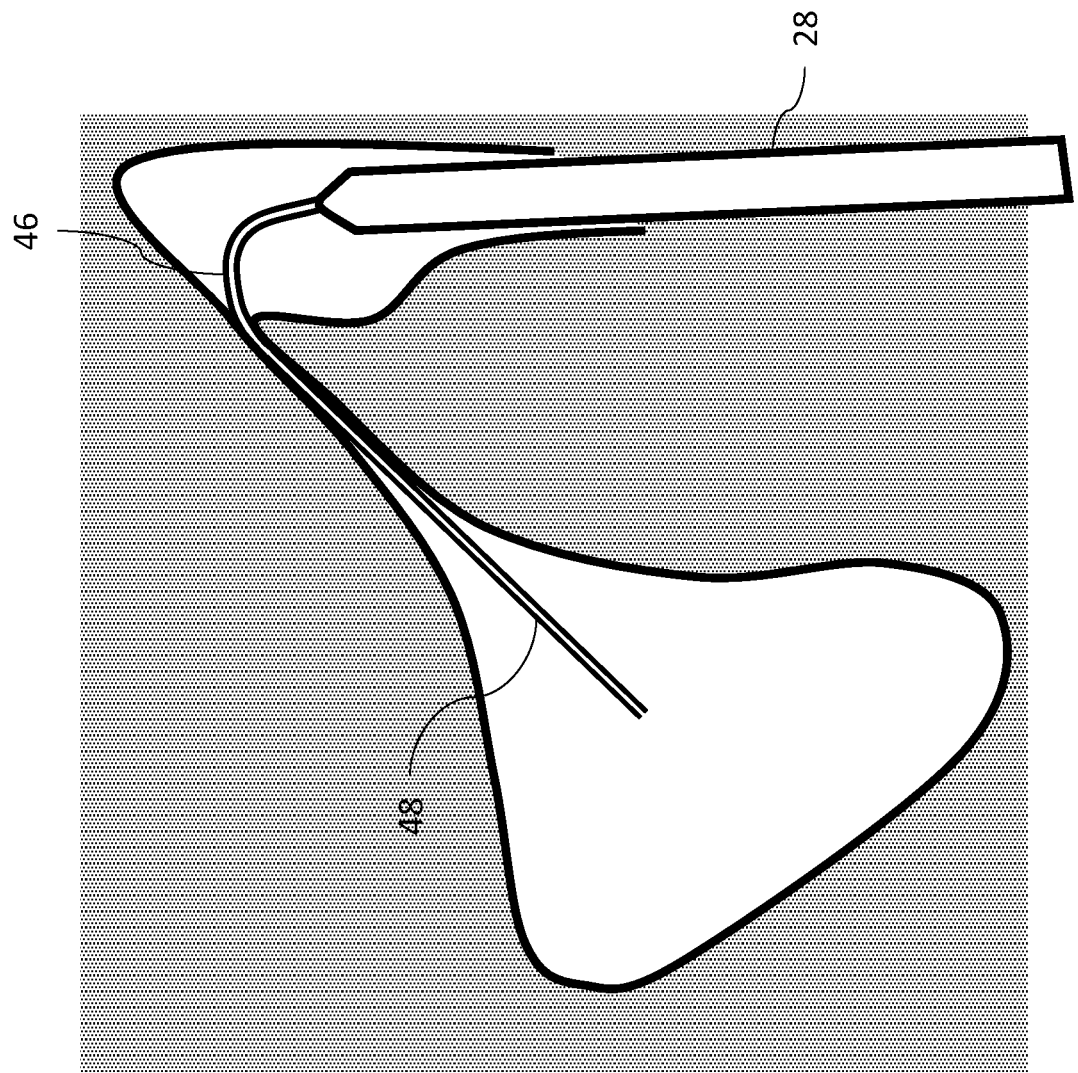
FIG. 4 is a schematic view of the medical instrument of FIG. 3 showing a guidewire of the medical instrument being extended into the body-part.

Reference is now made to FIG. 4, which is a schematic view of the medical instrument 28 of FIG. 3 showing a guidewire 48 of the medical instrument 28 being extended into the body-part. The guidewire 48 is extended from within the guide 46 into the body-part. The guidewire 48 generally extends in the direction in which the distal end of the guide 46 was fixed.

Figure 5:
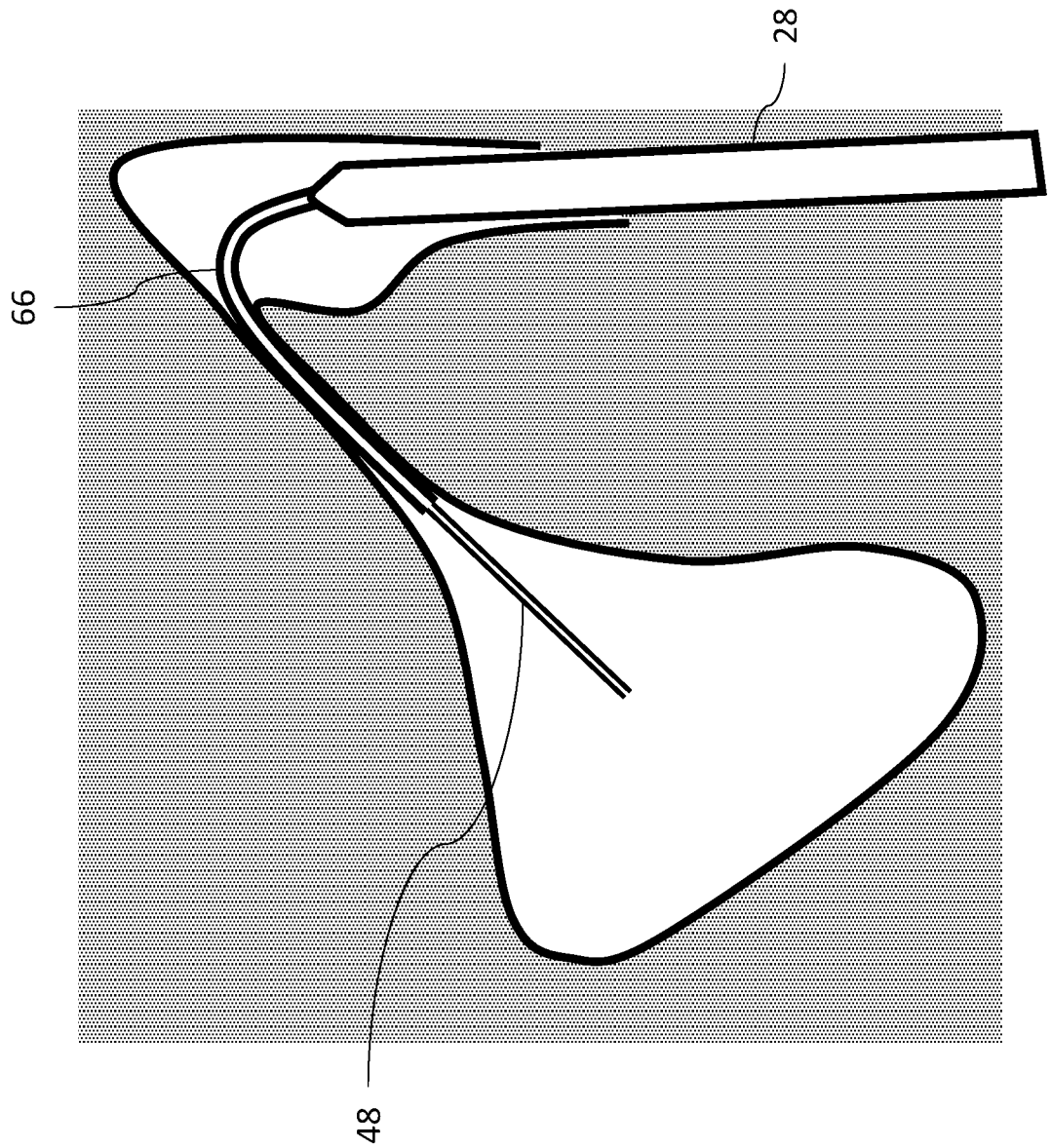
FIG. 5 is a schematic view of a balloon device being extended over the guidewire of FIG. 4.

Reference is now made to FIG. 5, which is a schematic view of a balloon device 66 of the medical instrument 28 being extended over the guidewire 48 of FIG. 4. In FIG. 5, the balloon device 66 is shown with its balloon deflated. The balloon device 66 is described in more detail with reference to FIGS. 6 and 7 below.

Figure 6:
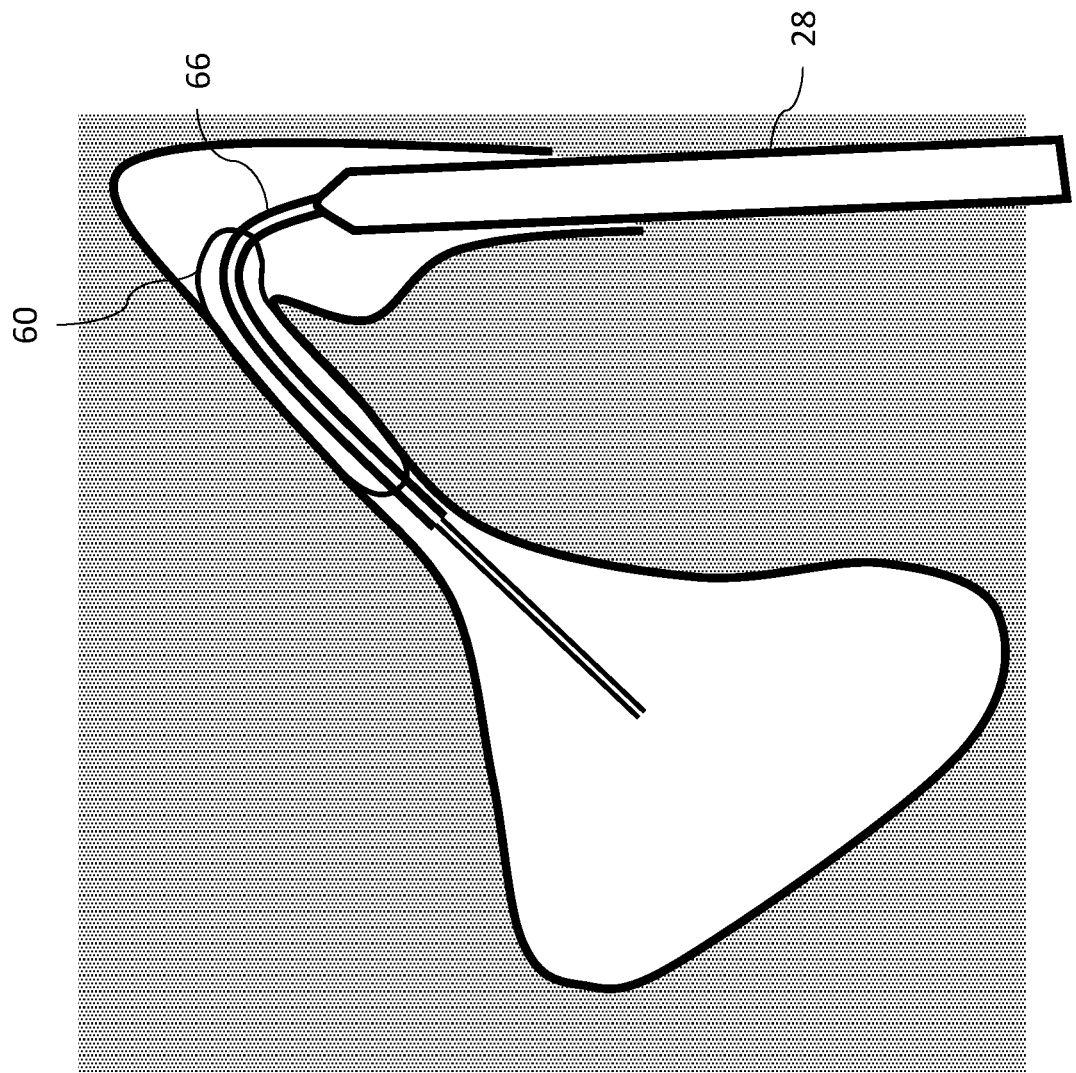
FIG. 6 is a schematic view of an inflatable balloon of the balloon device of FIG. 5 being inflated.

Reference is now made to FIG. 6, which is a schematic view of the inflatable balloon 60 of the balloon device 66 of FIG. 5 being inflated. The inflatable balloon 60 may be inflated for any suitable medical procedure. In the example of FIG. 6 the inflatable balloon 60 is inflated to perform a sinus dilation. The inflatable balloon 60 may be inflated using any suitable method for example, using air or a liquid such as saline. A suitable base design for the medical instrument 28 may be based on the RELIEVA SCOUT® Multi-Sinus Dilation System produced by Acclarent, Inc., of Irvine, Calif., USA. The medical instrument 28 has been described herein as an ENT tool with the inflatable balloon 60. The medical instrument 28 may be any suitable medical instrument for use in any suitable body-part of a living subject.

Figure 7:
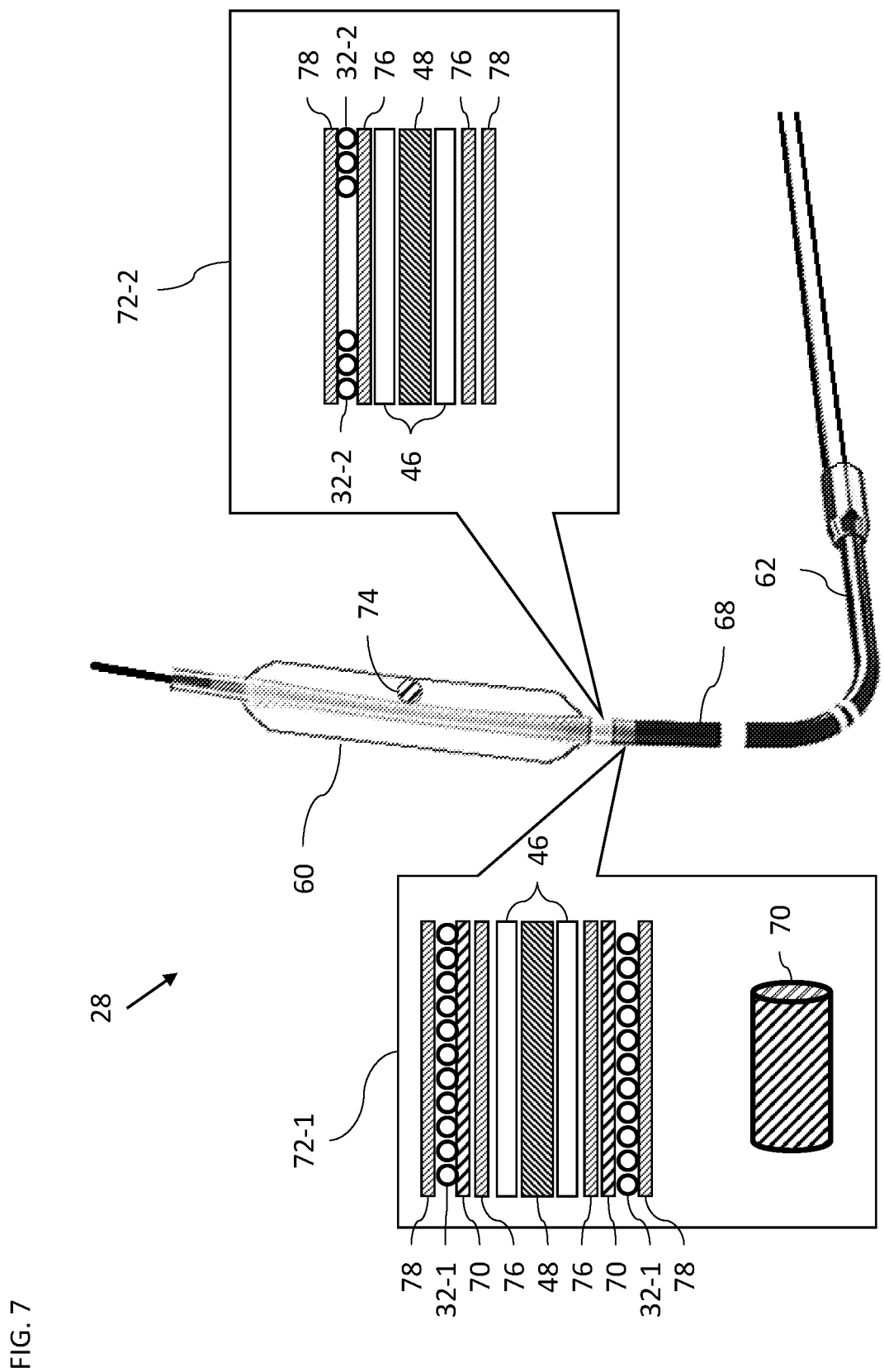
FIG. 7 is a schematic view of the medical instrument of FIG. 6 including cross-sectional views of transducers of the medical instrument.

Reference is now made to FIG. 7, which is a schematic view of the medical instrument 28 of FIG. 6 including cross-sectional views 72 of transducers 32 of the medical instrument 28. FIG. 7 includes two cross-sectional views 72, labeled 72-1 and 72-2. Both of the cross-sectional views 72-1 are longitudinal cross-sectional views, showing the various layers of the medical instrument 28.

The medical instrument 28 includes two position-tracking transducers 32 (labeled 32-1 and 32-2). The position-tracking transducer 32-1 may be a coil disposed coaxially with a shaft 68 of the medical instrument 28. The position-tracking transducer 32-2, which may be a coil, is disposed orthogonally to the position-tracking transducer 32-1. The position-tracking transducers 32-1, 32-2 together provide signals which may be used to compute a location and orientation including roll of the distal end 62 of the medical instrument 28. The position-tracking transducers 32 are shown as being disposed at a distal end of the inflatable balloon 60. In some embodiments, the position-tracking transducers 32 may be disposed at any suitable location on the medical instrument 28, for example, any suitable location of the shaft 68.

The medical instrument 28 includes a radiopaque marker 70 disposed on the shaft 68. In some embodiments, the radiopaque marker 70 includes a radiopaque cylinder as shown in FIG. 7. In some embodiments, the position-tracking transducer 32-1 is a coil, which is wound on the radiopaque cylinder.

The medical instrument 28 also includes a radiopaque marker 74 disposed on an element (e.g., comprised in the inflatable balloon 60) of the distal end 62 that is configured to extend away from the axis of the shaft 68.

The radiopaque markers 70, 74 may be comprised of any suitable radiopaque material, for example, but not limited to, stainless steel or iron, which is suitably coated with a biocompatible material.

The cross-sectional views 72-1, 72-1 shows that the guidewire 48 is disposed in the guide 46, and the guide 46 is surrounded by an inner layer 76 and an outer layer 78 of the balloon device 66 with the position-tracking transducers 32 sandwiched between the inner layer 76 and the outer layer 78.

The cross-sectional view 72-1 shows radiopaque marker 70 (e.g., the radiopaque cylinder) surrounding the inner layer 76 with the coil of the position-tracking transducer 32-1 being wound on the radiopaque marker 70 coaxially with the shaft 68. The cross-sectional view 72-2 shows the coil of the position-tracking transducer 32-2 wound orthogonally to the coil of the position-tracking transducer 32-1.

The radiopaque marker 70 may be conveniently disposed in the same location as the position-tracking transducer 32-1 for easier computation of the registration described below. In some embodiments, the position-tracking transducer 32-1 may be disposed in a different location from the radiopaque marker 70 and compensation between the given spatial relationship between the radiopaque marker 70 and the position-tracking transducer 32-1 is taken into account when performing the registration computations.

Figure 8:
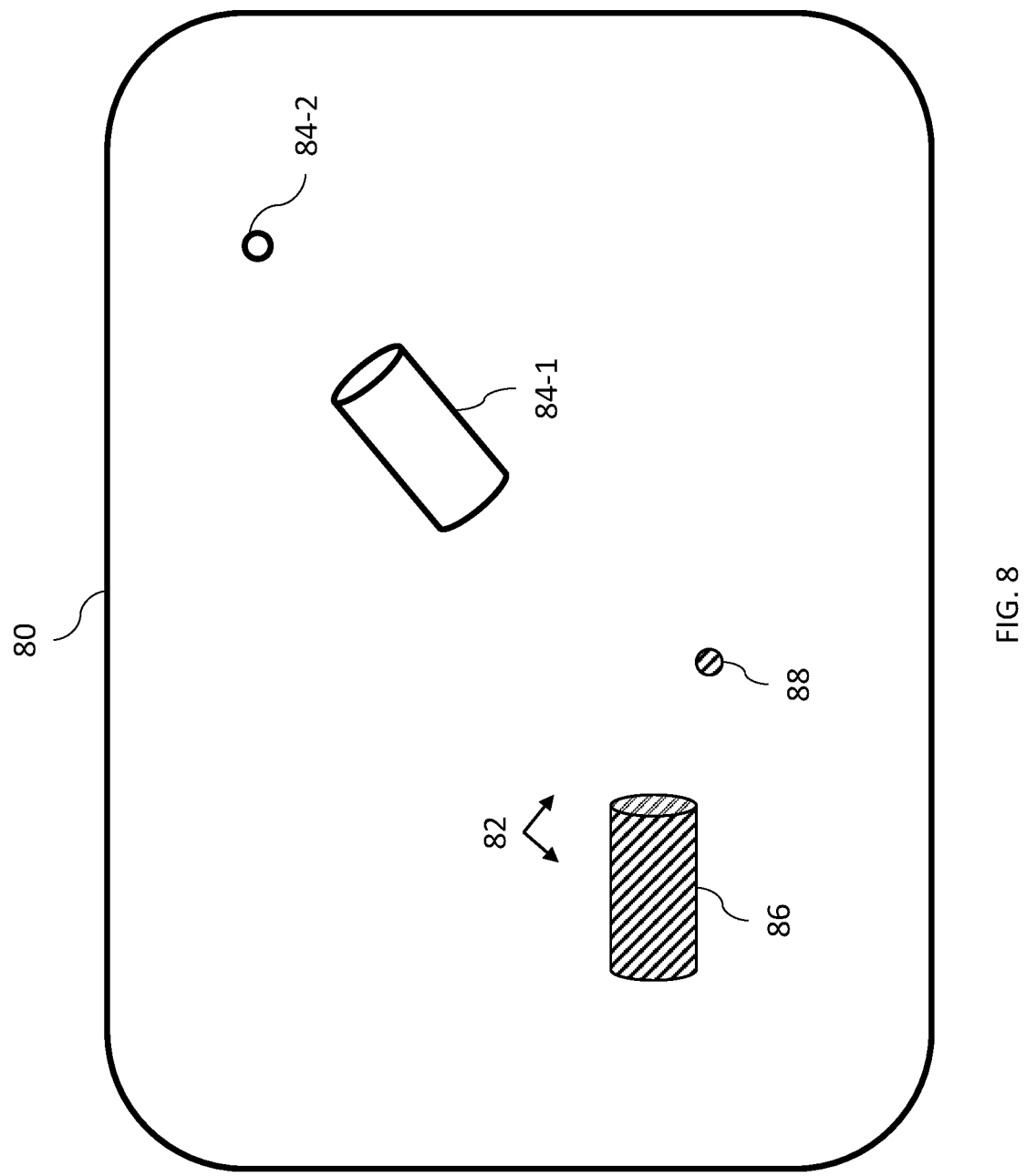
FIG. 8 is a schematic view a user interface screen including a captured fluoroscopic image and graphical representations indicative of computed positions of the distal end of the medical instrument.

Reference is now made to FIG. 8, which is a schematic view a user interface screen 80 including a captured fluoroscopic image 82 and graphical representations 84 (labeled 84-1 and 84-2) indicative of computed positions of the distal end 62 of the medical instrument 28. Reference is also made to FIG. 7. The captured fluoroscopic image 82 includes a marker-image 86 of the radiopaque marker 70 and a marker-image 88 of the radiopaque marker 74. The positioning of the graphical representation 84-1 in the user interface screen 80 corresponds to a computed location and orientation of the radiopaque marker 70 based on the signals provided by the position-tracking transducer 32-1. The positioning of the graphical representation 84-2 in the user interface screen 80 corresponds to a computed location of the radiopaque marker 74 based on the signals provided by the position-tracking transducer 32-2. The location of the radiopaque marker 74 may be computed based on a position around a circumference of the inflatable balloon 60 according to the computed roll of the position-tracking transducer 32-2 wherein the circumference also passes through the radiopaque marker 74.

As part of the registration process, the physician 54 manipulates the graphical representations 84 using the operating controls 51 so that the graphical representation 84-1 and the graphical representation 84-2 are aligned with the marker-image 86 and the marker-image 88, respectively. The physician 54 may manipulate the graphical representations 84 by moving them across the user interface screen 80 in any suitable direction (up, down, left, right, diagonal etc.), moving them backwards, moving them forwards, and changing the orientation and rotation (roll) of the graphical representations 84. As the graphical representations 84 correspond to different positions (e.g., the radiopaque marker 70 and the radiopaque marker 74) on the same item (e.g., the medical instrument 28), the graphical representations 84 are automatically moved together maintaining a same spatial relationship between the graphical representations 84. Nevertheless, it may be more intuitive for the physician 54 to try to align the cylinders (e.g., the graphical representation 84-1 with the marker-image 86) initially and then align the graphical representation 84-2 with the marker-image 88 afterwards.

Figure 9:
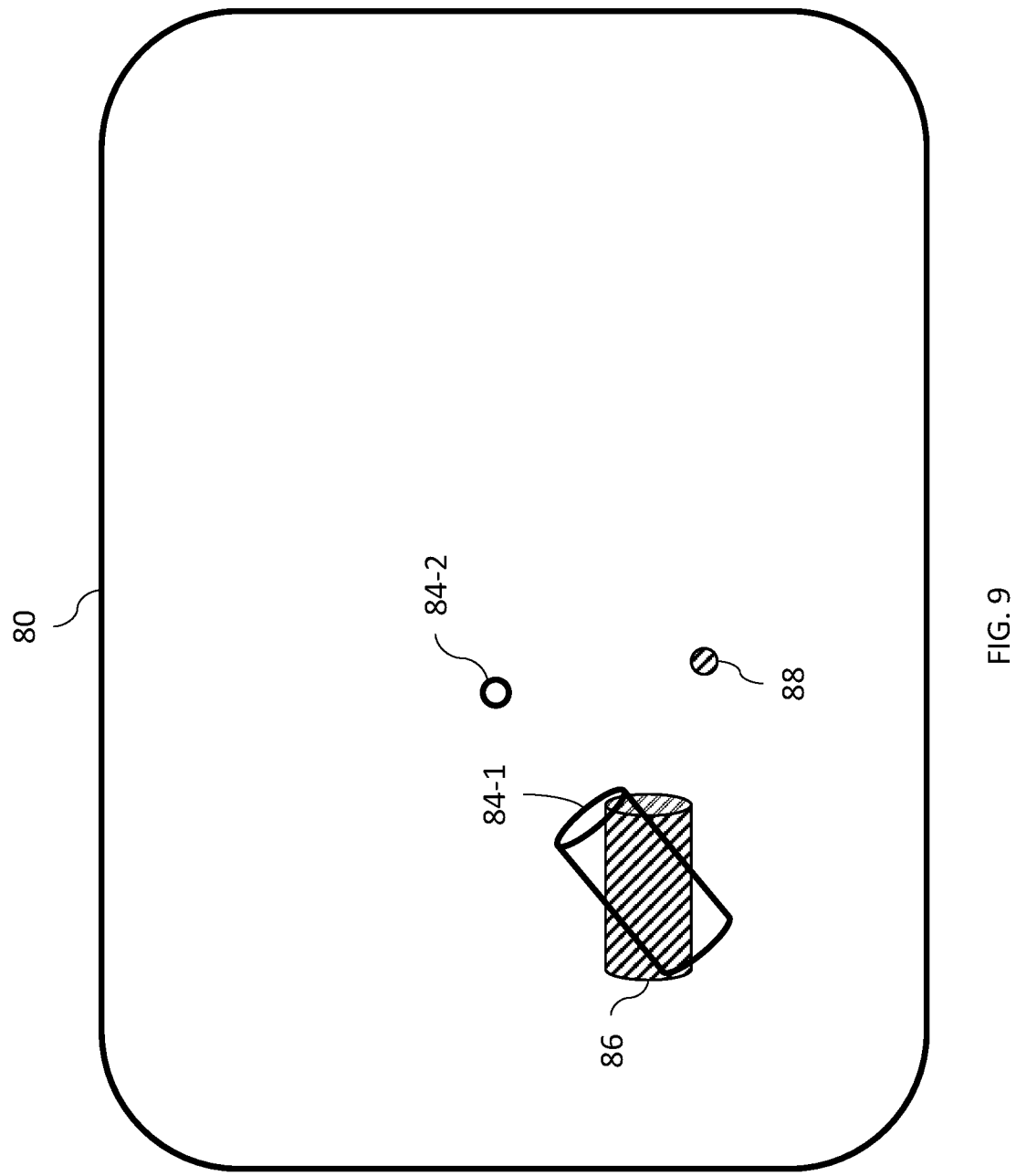
FIG. 9 is a schematic view of the user interface screen of FIG. 8 after an initial user alignment of the graphical representations.

Reference is now made to FIG. 9, which is a schematic view of the user interface screen 80 of FIG. 8 after an initial user alignment of the graphical representations 84. FIG. 9 shows that the graphical representations 84 have been moved closer to the marker-image 86 and the marker-image 88.

Figure 10:
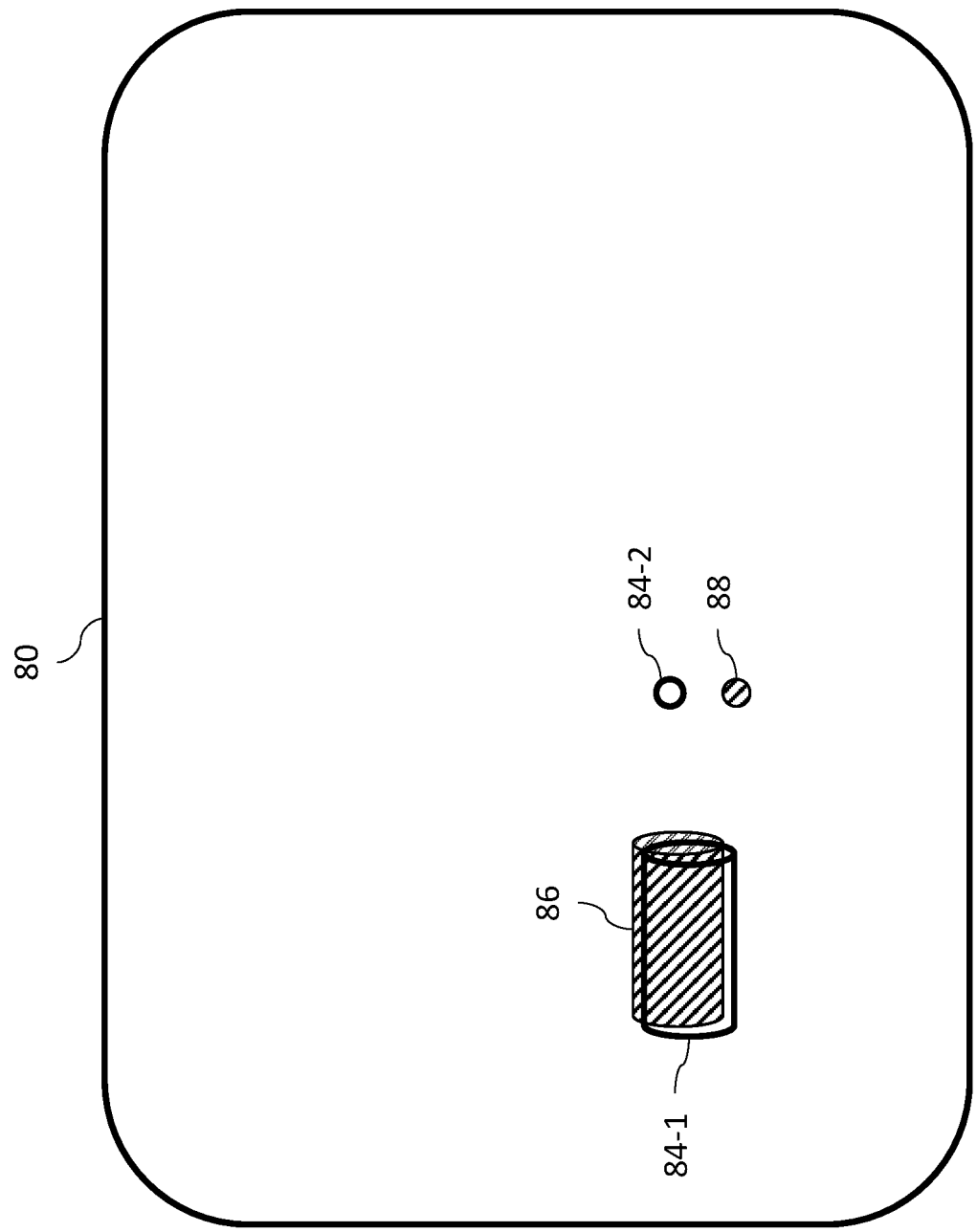
FIG. 10 is a schematic view of the user interface screen of FIG. 9 after a further user alignment of the graphical representations.

Reference is now made to FIG. 10, which is a schematic view of the user interface screen 80 of FIG. 9 after a further user alignment of the graphical representations 84. FIG. 10 shows that the graphical representation 84-1 has been rotated clockwise and is almost aligned with the marker-image 86, but the graphical representation 84-2 is still misaligned with the marker-image 88.

Figure 11:
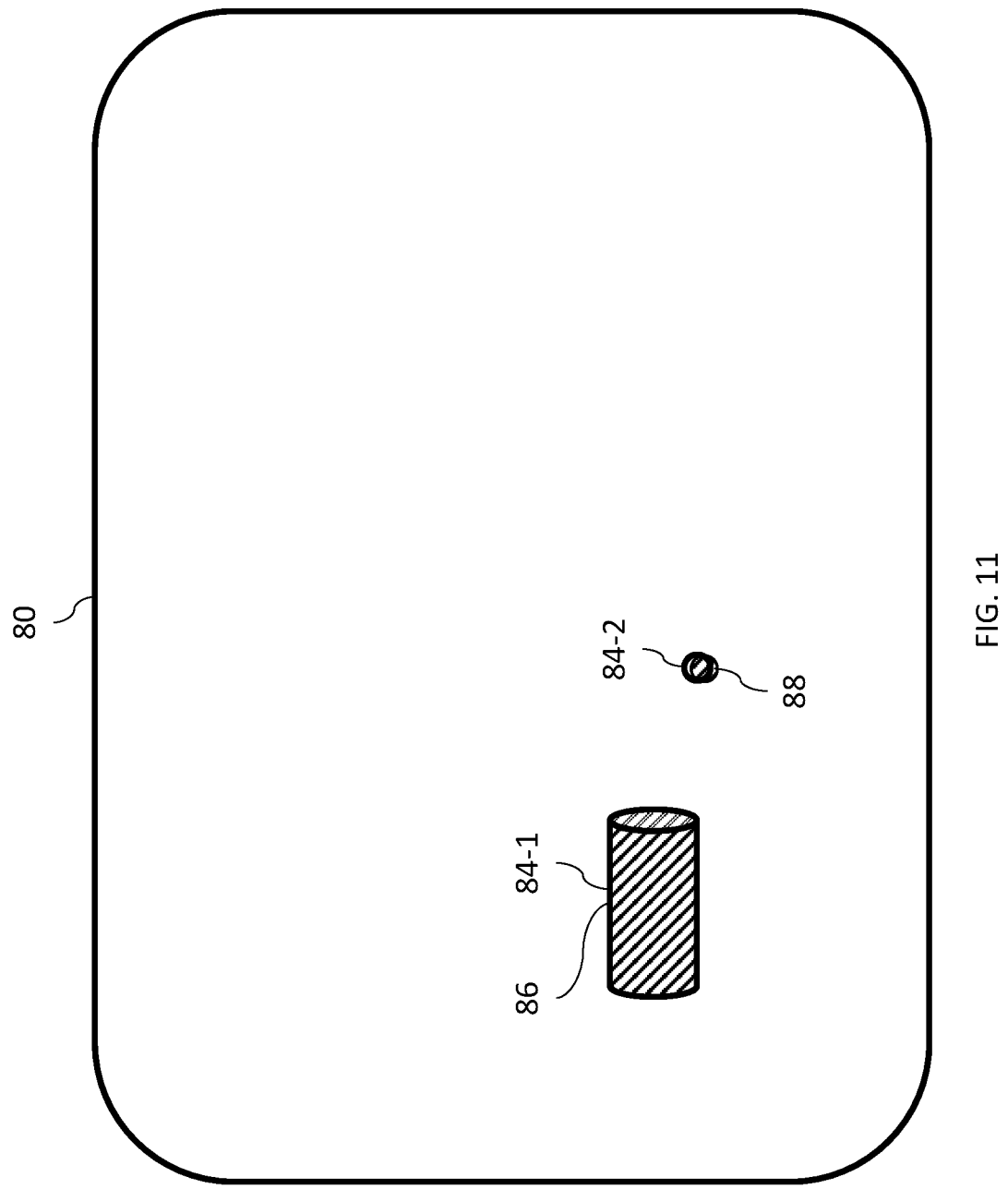
FIG. 11 is a schematic view of the user interface screen of FIG. 10 after yet further user alignment of the graphical representations.

Reference is now made to FIG. 11, which is a schematic view of the user interface screen 80 of FIG. 10 after yet further user alignment of the graphical representations 84. The graphical representations 84 have been rotated around the axis of the graphical representation 84-1 until the graphical representation 84-2 is almost aligned with the marker-image 88. Once the graphical representations 84-1, 84-2 are aligned with the marker-image 86 and the marker-image 88, respectively, the user alignment inputs are used to register the coordinate frame of the fluoroscope 40 with the coordinate frame of the position-tracking sub-system 64 (FIG. 2).

Figure 12:
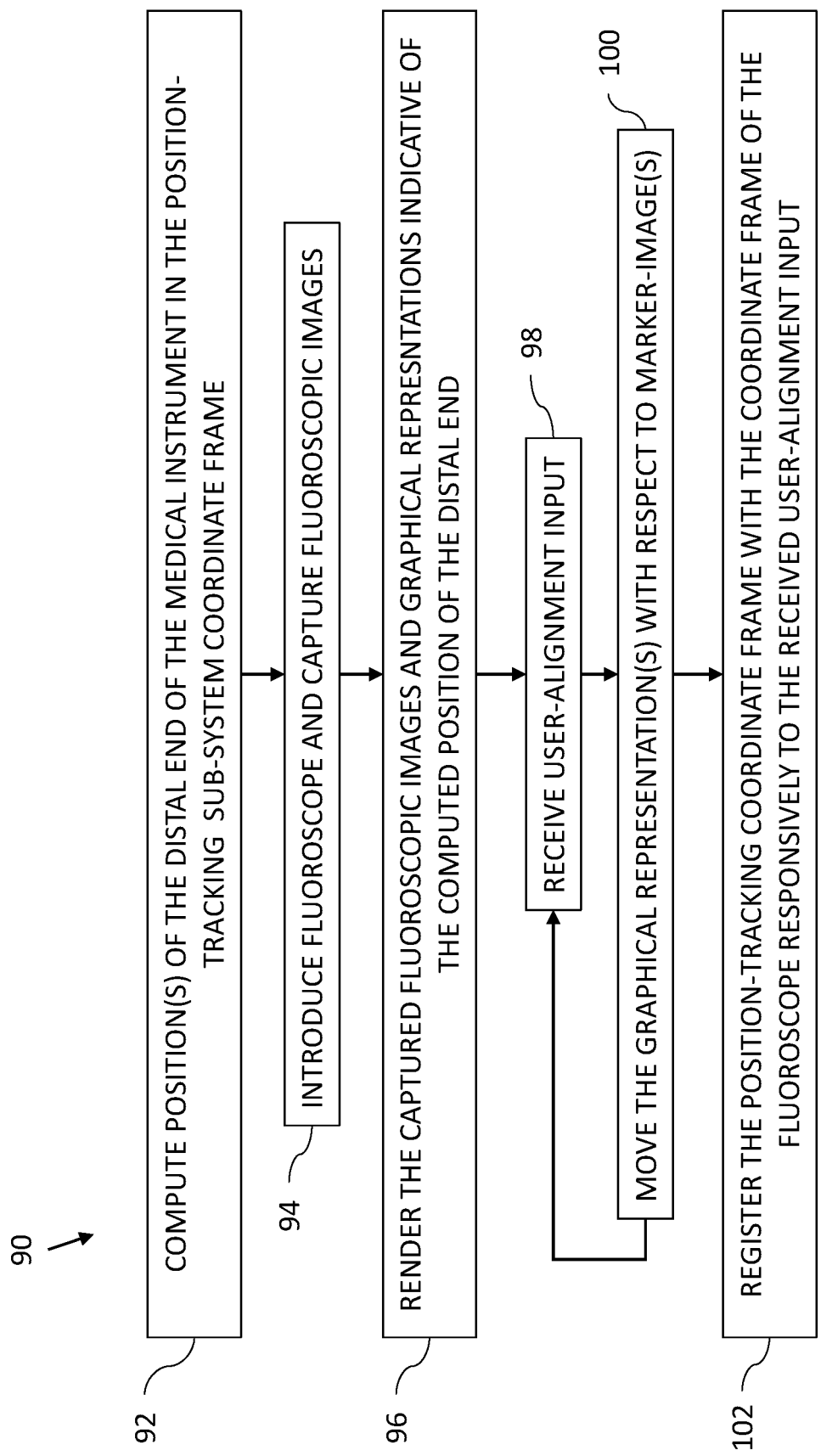
FIG. 12 is a flowchart including exemplary steps in a registration method for use in the system of FIG. 1.

Reference is now made to FIG. 12, which is a flowchart 90 including exemplary steps in a registration method for use in the system 20 of FIG. 1. The position-tracking sub-system 64 (FIG. 2) is configured to compute (block 92) a position including at least one location and an orientation (including roll) of the distal end 62 of the medical instrument 28 in a position-tracking sub-system coordinate frame responsively to the position signals provided by the position-tracking transducers 32 (FIG. 7).

In some embodiments, the position tracking sub-system 64 is configured to compute: a first position including a first location and an orientation (e.g., of the radiopaque marker 70) of the distal end 62 of the medical instrument 28 in the position-tracking sub-system coordinate frame responsively to the position signal provided by the position-tracking transducer 32-1; and a second position including a second location (e.g., of the radiopaque marker 74) of the distal end 62 of the medical instrument 28 in the position-tracking sub-system coordinate frame responsively to the position signal provided by the position-tracking transducer 32-2.

The fluoroscope 40 is introduced and is configured to capture (block 94) fluoroscopic images of an interior of the body part and the radiopaque markers 70, 74 of the medical instrument 28 over time.

The registration sub-system 44 is configured to render (block 96), to the display 56, the captured fluoroscopic images including the marker-image 86 of the radiopaque marker 70 and the marker-image 88 of the radiopaque marker 74, and superimpose over the fluoroscopic images, the graphical representations 84 at positions indicative of the computed position(s) of the distal end 62 (e.g., the graphical representation 84-1 at the first computed position and the graphical representations 84-2 at the second computed position).

The registration sub-system 44 is configured to receive (block 98) user-alignment input aligning the respective graphical representations 84 with the respective ones of the marker-images 86, 88 (e.g., aligning the graphical representation 84-1 with the marker-image 86 and the graphical representation 84-2 with the marker-image 88. The registration sub-system 44 is configured to move (block 100) the graphical representations 84 with respect to the marker-images 86, 88 on the user interface screen 80 (FIGS. 8-11) according to the received user-alignment input. The steps of blocks 98 and 100 may repeated to allow for multiple updates to the movement of the graphical representations 84 on the user interface screen 80.

The registration sub-system 44 is configured to register (block 102) the position-tracking sub-system coordinate frame with a coordinate frame of the fluoroscope 40 responsively to the received user-alignment input which brought the graphical representations 84 from their original position to their final position aligned with the marker-images 86, 88.

Once the position-tracking sub-system coordinate frame is registered with the coordinate frame of the fluoroscope 40, the processor 38 is configured to render to the display 56 the fluoroscopic images with a representation of the medical instrument 28 thereon.

Figure 13:
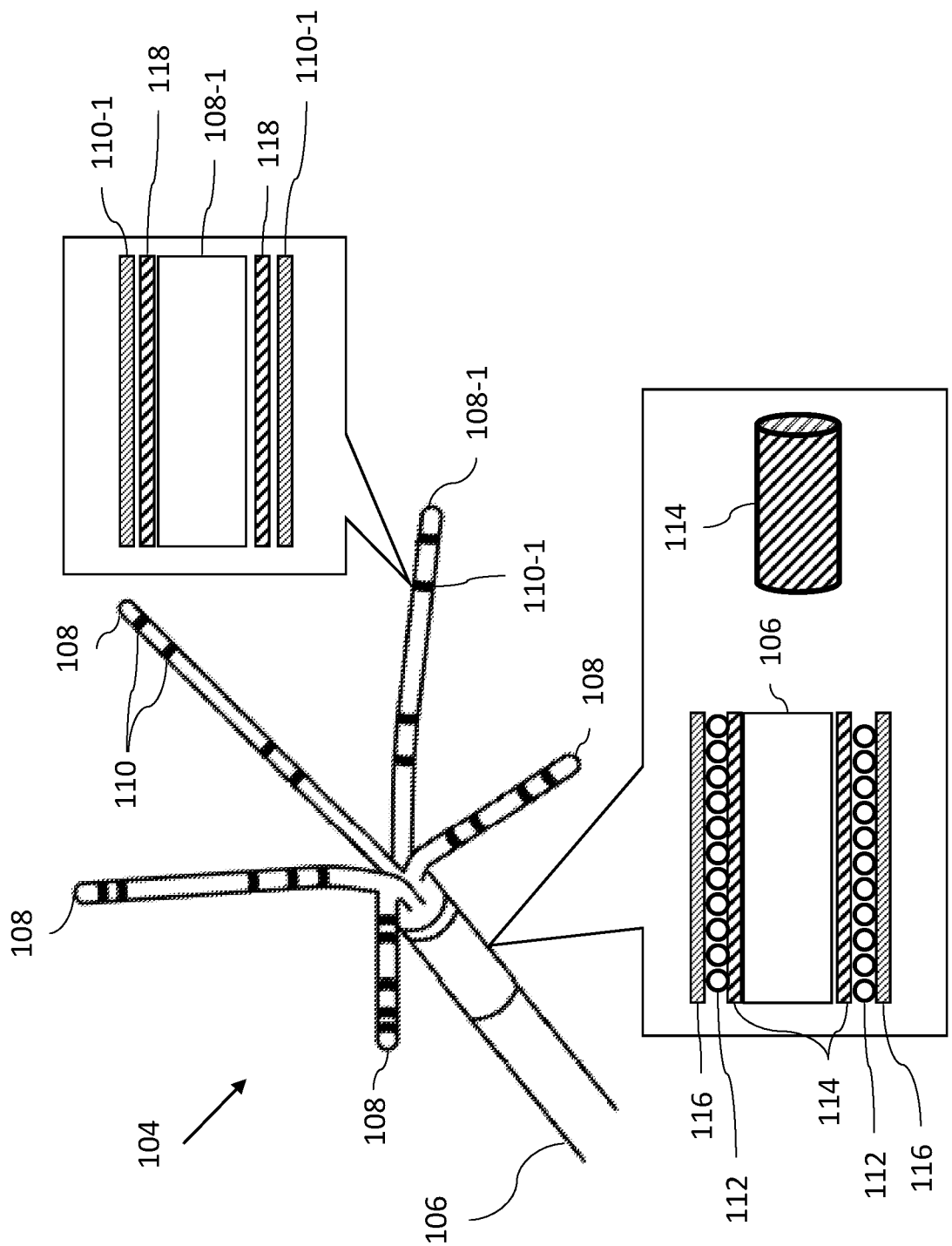
FIG. 13 is a schematic view of multi-prong probe for use with the system of FIG. 1.

Reference is now made to FIG. 13, which is a schematic view of multi-prong probe 104 for use with the system 20 of FIG. 1. The multi-prong probe 104 includes a shaft 106 and multiple prongs 108, each of the prongs 108 including a plurality of electrodes 110. Only some of the electrodes 110 have been labeled for the sake of simplicity. An example of the multi-prong probe 104 is the CARTO PENTARAY® catheter produced by Biosense Webster of 33 Technology Drive, Irvine, Calif. 92618 USA. The multi-prong probe 104 includes a coil 112 wound on a radiopaque cylinder marker 114 which is disposed on the shaft 106 and is coaxial with the shaft 106. The coil 112 is covered with an outer layer 116. The coil 112 is configured as a position-tracking transducer and provides a position signal to the position-tracking sub-system 64 (FIG. 2) in order to compute a location and orientation of the radiopaque cylinder 114.

One of the electrodes 110, an electrode 110-1, of one of the prongs 108, a prong 108-1 is disposed over a radiopaque layer marker 118 over the prong 108-1 and is therefore co-located with the radiopaque layer marker 118. The prong 108-1 is an elongated element which is configured to extend away from the axis of the shaft 106. The electrode 110-1 may be used as a position-tracking transducer to provide a position signal to the position-tracking sub-system 64 in order to compute a position (e.g., location) of the radiopaque layer 118 which allows a roll of the multi-prong probe 104 to be registered.

Figure 14:
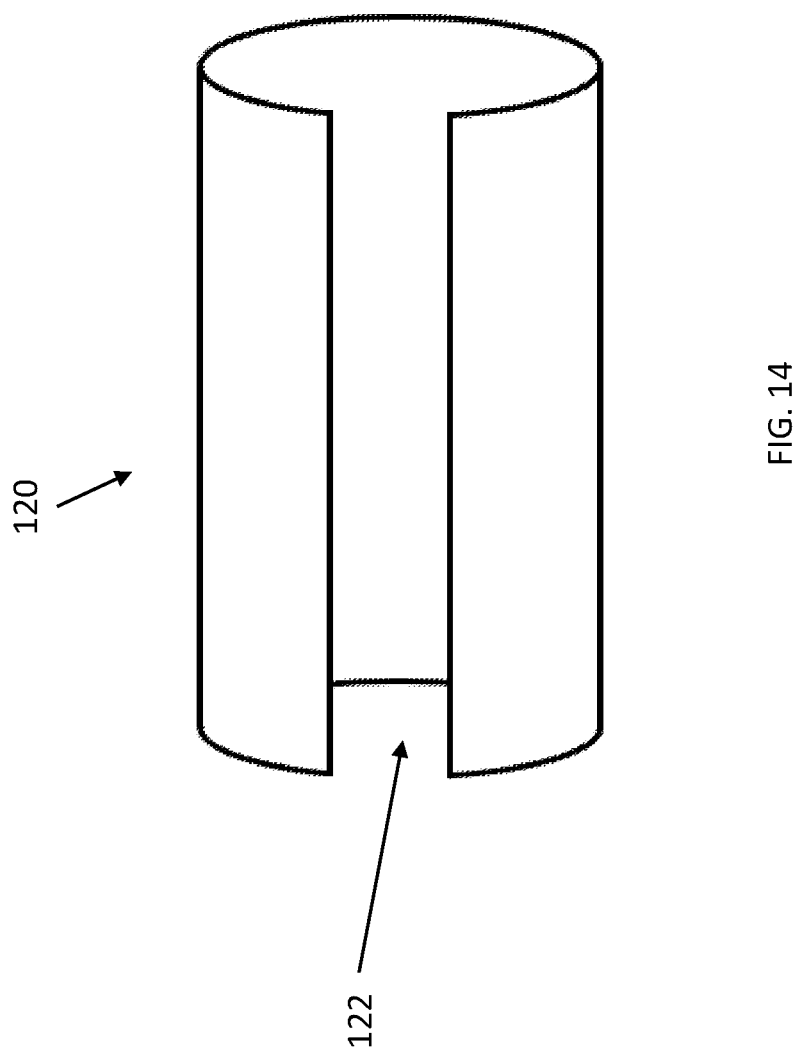
FIG. 14 is a schematic view of an alternative radiopaque marker for use in the system of FIG. 1.

Reference is now made to FIG. 14, which is a schematic view of an alternative radiopaque marker 120 for use in the system 20 of FIG. 1. In some embodiments, the single radiopaque marker 120 replaces the cylindrical radiopaque marker of FIG. 7, and may be used to align location, orientation including roll. For example, the single radiopaque marker 120 may include a cylinder with a longitudinal gap 122. A cylinder with a similarly sized longitudinal gap defined by a location and orientation (including roll) computed from signals provided by the coaxial coil 32-1 (FIG. 7) and the orthogonally placed coil 32-2 (FIG. 7) is superimposed over one of the fluoroscopic images in the user interface screen 80 (FIGS. 8-11). The physician 54 then manipulates the superimposed cylinder with respect to the marker-image of the radiopaque cylinder in order to align the cylinders including the longitudinal gaps of the cylinders. The user alignment input defines the differences between the fluoroscope coordinate frame and the position-tracking sub-system coordinate frame with respect to location and orientation including roll. The user alignment input is then used to register the two coordinate frames with each other.

Various features of the invention which are, for clarity, described in the contexts of separate embodiments may also be provided in combination in a single embodiment. Conversely, various features of the invention which are, for brevity, described in the context of a single embodiment may also be provided separately or in any suitable sub-combination.

The embodiments described above are cited by way of example, and the present invention is not limited by what has been particularly shown and described hereinabove. Rather the scope of the invention includes both combinations and subcombinations of the various features described hereinabove, as well as variations and modifications thereof which would occur to persons skilled in the art upon reading the foregoing description and which are not disclosed in the prior art.

What is claimed is:

1. A medical procedure system, comprising:
   (a) a medical instrument configured to be inserted into a body part of a living subject, and comprising:
   position-tracking transducers configured to provide position signals;
   iii) a shaft;
   (iii) a distal end; and
   (iv) at least one radiopaque marker;
   (b) a position tracking sub-system configured to compute a position including at least one location and an orientation of the distal end of the medical instrument in a position-tracking sub-system coordinate frame responsively to the position signals;
   (c) a fluoroscope configured to capture fluoroscopic images of an interior of the body part and the at least one radiopaque marker of the medical instrument over time, wherein the captured fluoroscopic images include at least one marker-image of the at least one radiopaque marker;
   (d) a display; and
   (e) a registration sub-system configured to:
   (i) render, to the display, the captured fluoroscopic images including, and at least one graphical representation indicative of the computed position of the distal end;
   (ii) receive user-alignment input aligning the at least one graphical representation with the at least one marker-image; and
   (iii) register the position-tracking sub-system coordinate frame with a coordinate frame of the fluoroscope responsively to the received user-alignment input.

2. The system according to claim 1, wherein:
   (a) the distal end includes an element which is configured to extend away from an axis of the shaft;
   (b) the at least one radiopaque marker includes:
   (i) a first radiopaque marker disposed on the shaft; and
   (iii) a second radiopaque marker disposed on the element which is configured to extend away from the axis of the shaft;
   (c) the position tracking sub-system is configured to compute:
   (i) a first position including a first location and an orientation of the distal end of the medical instrument in the position-tracking sub-system coordinate frame responsively to at least one of the position signals; and
   (ii) a second position including a second location of the distal end of the medical instrument in the position-tracking sub-system coordinate frame responsively to at least one of the position signals; and
   (d) the registration sub-system is configured to:
   (i) render, to the display,
      (A) the captured fluoroscopic images including a first marker-image of the first radiopaque marker,
      (B) a second marker-image of the second radiopaque marker,
      (C) a first graphical representation indicative of the computed first position of the distal end, and
      (D) a second graphical representation indicative of the computed second position of the distal end; and
   (ii) receive user-alignment input aligning the first graphical representation with the first marker-image, and the second graphical representation with the second marker-image.

3. The system according to claim 2, wherein the position-tracking transducers include a first coil disposed coaxially with the shaft.

4. The system according to claim 3, wherein the first radiopaque marker includes a radiopaque cylinder.

5. The system according to claim 4, wherein the first coil is wound on the radiopaque cylinder.

6. The system according to claim 5, wherein the position-tracking transducers includes a second coil disposed orthogonally to the first coil.

7. The system according to claim 3, wherein the element which is configured to extend away from the axis of the shaft is comprised in an inflatable balloon.

8. The system according to claim 7, wherein the first radiopaque marker includes a radiopaque cylinder, the first coil being wound on the radiopaque cylinder, and the position-tracking transducers include a second coil disposed orthogonally to the first coil.

9. The system according to claim 3, wherein the element which is configured to extend away from the axis of the shaft is comprised in an elongated element comprising an electrode.

10. The system according to claim 9, wherein the position-tracking transducers include the electrode.

11. The system according to claim 10, wherein the second radiopaque marker is co-located with the electrode.

12. The system according to claim 1, wherein the at least one radiopaque marker includes a cylinder with a longitudinal gap.

13. A medical procedure method, comprising:
    (a) inserting a medical instrument into a body part of a living subject;
    (b) computing a first position including a first location and an orientation of a distal end of the medical instrument in a position-tracking sub-system coordinate frame responsively to position signals provided by position-tracking transducers of the medical instrument;
    (c) capturing, using a fluoroscope, fluoroscopic images of an interior of the body part and at least one radiopaque marker of the medical instrument over time, wherein the captured fluoroscopic images include at least one marker-image of the at least one radiopaque marker;
    (d) rendering, to a display, the captured fluoroscopic images, and at least one graphical representation indicative of the computed first position of the distal end;
    (e) receiving user-alignment input aligning the at least one graphical representation with the at least one marker-image; and
    (f) registering the position-tracking sub-system coordinate frame with a coordinate frame of the fluoroscope responsively to the received user-alignment input.

14. The method according to claim 13, wherein:
    (a) the distal end includes an element which is configured to extend away from an axis of a shaft of the medical instrument;
    (b) the at least one radiopaque marker includes:
    (i) a first radiopaque marker disposed on the shaft; and
    (ii) a second radiopaque marker disposed on the element which is configured to extend away from the axis of the shaft;

the method further comprising:
computing a first position including a first location and an orientation of the distal end of the medical instrument in the position tracking sub system coordinate frame responsively to at least one of the position signals;
(a) computing a second position including a second location of the distal end of the medical instrument in the position-tracking sub-system coordinate frame responsively to at least one of the position signals;
(b) rendering, to the display, the captured fluoroscopic images including:
 (i) a first marker-image of the first radiopaque marker,
 (ii) a second marker-image of the second radiopaque marker,
 (iii) a first graphical representation indicative of the computed first position of the distal end, and
 (iv) a second graphical representation indicative of the computed second position of the distal end; and
(c) receiving user-alignment input aligning the first graphical representation with the first marker-image, and the second graphical representation with the second marker-image.

15. The method according to claim 14, wherein the position-tracking transducers include a first coil disposed coaxially with the shaft.

16. The method according to claim 15, wherein the first radiopaque marker includes a radiopaque cylinder.

17. The method according to claim 16, wherein the first coil is wound on the radiopaque cylinder.

18. The method according to claim 17, wherein the position-tracking transducers includes a second coil disposed orthogonally to the first coil.

19. The method according to claim 15, wherein the element which is configured to extend away from the axis of the shaft is comprised in an inflatable balloon.

20. The method according to claim 19, wherein the first radiopaque marker includes a radiopaque cylinder, the first coil being wound on the radiopaque cylinder, and the position-tracking transducers include a second coil disposed orthogonally to the first coil.

21. The method according to claim 15, wherein the element which is configured to extend away from the axis of the shaft is comprised in an elongated element comprising an electrode.

22. The method according to claim 21, wherein the position-tracking transducers include the electrode.

23. The method according to claim 22, wherein the second radiopaque marker is co-located with the electrode.

24. The method according to claim 13, wherein the at least one radiopaque marker includes a cylinder with a longitudinal gap.

* * * * *